United States Patent [19]

Wakatake et al.

[11] Patent Number: 4,774,055

[45] Date of Patent: Sep. 27, 1988

[54] AUTOMATIC ANALYSIS APPARATUS

[75] Inventors: Kouichi Wakatake, Koganei; Takejirou Yokosuka, Hino; Hidehiko Fujioka, Tama; Teruo Mochida, Hino; Kazutomi Yokota, Akigawa, all of Japan

[73] Assignee: Japan Tectron Instruments Corporation, Tokyo, Japan

[21] Appl. No.: 877,441

[22] Filed: Jun. 23, 1986

[30] Foreign Application Priority Data

| Jun. 26, 1985 | [JP] | Japan | 60-139553 |
| Feb. 20, 1986 | [JP] | Japan | 61-36230 |
| Feb. 24, 1986 | [JP] | Japan | 61-38603 |
| Mar. 19, 1986 | [JP] | Japan | 61-61673 |
| Apr. 2, 1986 | [JP] | Japan | 61-76122 |
| Apr. 11, 1986 | [JP] | Japan | 61-83851 |

[51] Int. Cl.⁴ ............................................. G01N 35/04
[52] U.S. Cl. ......................................... 422/64; 422/63; 422/73; 422/100; 422/69; 436/807
[58] Field of Search ........................... 422/64, 71, 73, 63, 422/67, 69; 436/45, 71; 141/130

[56] References Cited

U.S. PATENT DOCUMENTS

| 4,101,284 | 7/1978 | Defiglio et al. | 422/100 |
| 4,268,477 | 5/1981 | Herystark | 422/64 |
| 4,271,123 | 6/1981 | Curry et al. | 422/67 |
| 4,276,051 | 6/1981 | Ginsberg et al. | 422/64 |
| 4,313,735 | 2/1982 | Yamashita et al. | 422/64 |
| 4,325,910 | 4/1982 | Jordan | 422/64 |
| 4,338,279 | 7/1982 | Orimo et al. | 422/64 |
| 4,383,041 | 5/1983 | Kutsusawa et al. | 422/63 |
| 4,483,823 | 11/1984 | Umetsu et al. | 422/64 |

Primary Examiner—Michael S. Marcus
Attorney, Agent, or Firm—Eric P. Schellin

[57] ABSTRACT

An automatic analysis apparatus is disclosed which provides for various analytical operations in clinical diagnosis and experiments including measuring the changes in light absorbance of a large number of samples mixed with different reagents in a progressive manner, biochemical, electrolytical, fluorescence, and immunological analysis and EIA analysis of samples in bead solid phase. A plurality of samples are maintained, together with diluents and emergency samples, in an ordered sequence on a sample table rotatably disposed which is rotated by drive means in a stepping manner to move the samples progressively to a predetermined suction position at which a sample pipetter picks up a measured amount of sample and dispenses it to one of a plurality of reaction containers that are arranged in an ordered sequence on a reaction table rotatably disposed, preferably about said sample table. A first and a second reagent table are provided, each carrying a plurality of reagents different in kind from one another, selected for various analyses to be performed. A first and a second reagent pipetter are provided and operated to pick up a measured amount of a particular reagent and mix it with any selected sample in the reaction containers. Each sample and reagent mixture may be scanned to measure the rate of light absorbance during a period of time as the reaction containers is rotated on the reaction table a photometer system including a rotating frame carrying thereon filters for different wavelengths through which the optical beam from a light source is passed to traverse the reaction container to be sensed by an optical sensor as the reaction container is rotated. Each reagent pipetting tube is provided with agitator means which is operated, after each dispensing operation of the pipetting tube into the reaction container, to stir the mixture in the reaction container into a homogenous state for proper reaction.

4 Claims, 11 Drawing Sheets

AUTOMATIC ANALYSIS APPARATUS

BACKGROUND OF THE INVENTION (1) Field of the Invention

The present invention relates in general to an automatic analysis apparatus and, in particular, to such a device which is capable of various analytical operations accurately at high speed, such as biochemical analysis, immunological analysis, determining the drug content in blood, and electrolytic analysis.

(2) Description of the Prior Art

Various types of automatic analyses apparatus have been proposed, in which a sample is mixed with a reagent in order to observe the resultant reaction in an automatic manner. One such an example is disclosed in Japanese laid-open patent application No. 60-139553, which is consists of a number of sample containers each containing a discrete sample arranged, together with diluent supply pipes, on a sample table, a number of reaction vessels laid on a reaction table rotatably disclosed around the sample table, a first and second group of reagents orderly set on a first and second reagent table, respectively, a sampling device for dispensing a sample from the sample table into one or more of the vessels on the reaction table, a first and second reagent dispensing mechansm each adapted to dispense a reagent from the reagent tables into the samples in the reaction vessels sequentially, and a photometric means for measuring the changes of the mixtures in them during a period of time by colorimetry.

However, this typical apparatus has been proved to be desirably fast and efficient in handling a large number of samples with proper identification of the reaction vessels for reagent dispensing. In addition, the photometer means requires means to adjust the intensity of light rays passed through filters, making the construction complicated. Furthermore, this apparatus cannot be used for other than biochemical analysis.

Other devices have been designed for limited purposes and might have been constructed complicated in mechanism and large in size with resultant increased costs to incorporate various analytical functions such as biochemical, immunological, and electrolytic analyses and measuring the drug content in blood into a single system, since they differ from one another in the sequence of handling samples in reaction with the reagents.

Another disadvantage of those conventional automatic analyses apparatus is the inability to keep a reagent under suitable condition until it is actually mixed with the sample. While some reagents used in enzyme analysis must be kept at strictly 2° to 10° C. and others are readily affected by high temperature, the environments in which they are used can be at high room temperature, deteriorating them.

It is this situation that gave rise to the present invention.

SUMMARY OF THE INVENTION

A primary object of the present invention is to provide an automatic analysis apparatus for clinical use capable of a variety of analytical operations such as biochemical, electrolytic, and immunological analyses and measuring the drug content in blood by homogenous system antigen-antibody or fluorescence method.

Another object of the present invention is to provide such a device capable of accurate operation at high speed.

A further object of the present invention is to provide such a device which is simple in construction and can accordingly be built at low costs.

An additional object of this invention is to provide such a device which is very easy to operate in distributing samples and reagents between a large number of reaction vessels.

A still other object of this invention is to provide such a device having means for controlling the temperature of reagents.

A further object of this invention is to provide such a device in which a sample can be tested with two or more reagents for different analyses in a successive manner.

An additional object is to provide such a device having means for stirring the contents of a reaction vessel into a homogenous state.

An additional object is to provide such a device which provides for biochemical and qualitative analyses by means of photometer means.

The above and other objects, features and advantages of the present invention will be more fully understood and appreciated from the following detailed description of specific embodiments taken together with the accompanying drawings in which similar parts are referred to by like reference characters.

BRIEF DESCRIPTION OF THE DRAWINGS

The invention will now be described in greater detail with respect to the automatic analysis apparatus according to the invention with reference to the drawing in which.

DETAILED DESCRIPTION OF THE PREFERRED EMBODIMENTS

Figure 1:
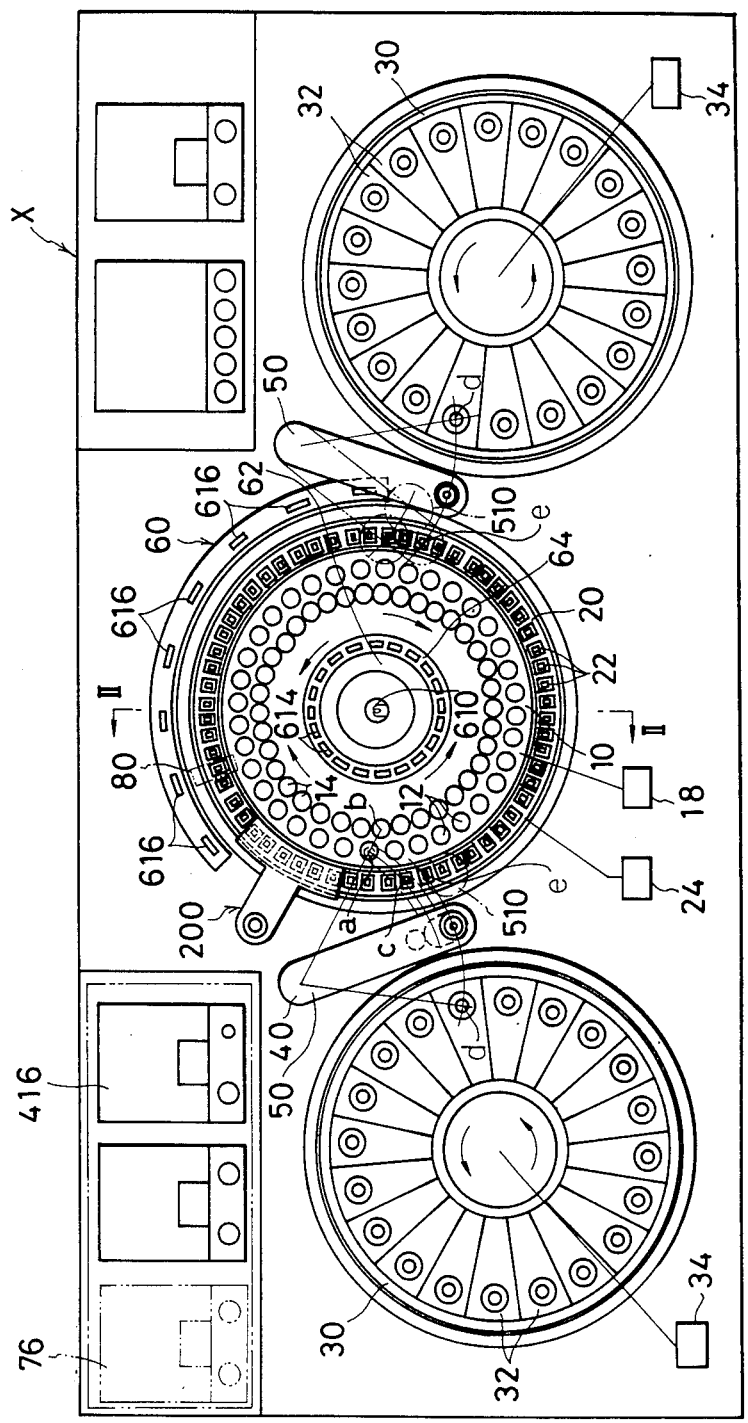
FIG. 1 is a plan view of a first preferred embodiment of the automatic analysis apparatus according to the present invention.
Figure 2:
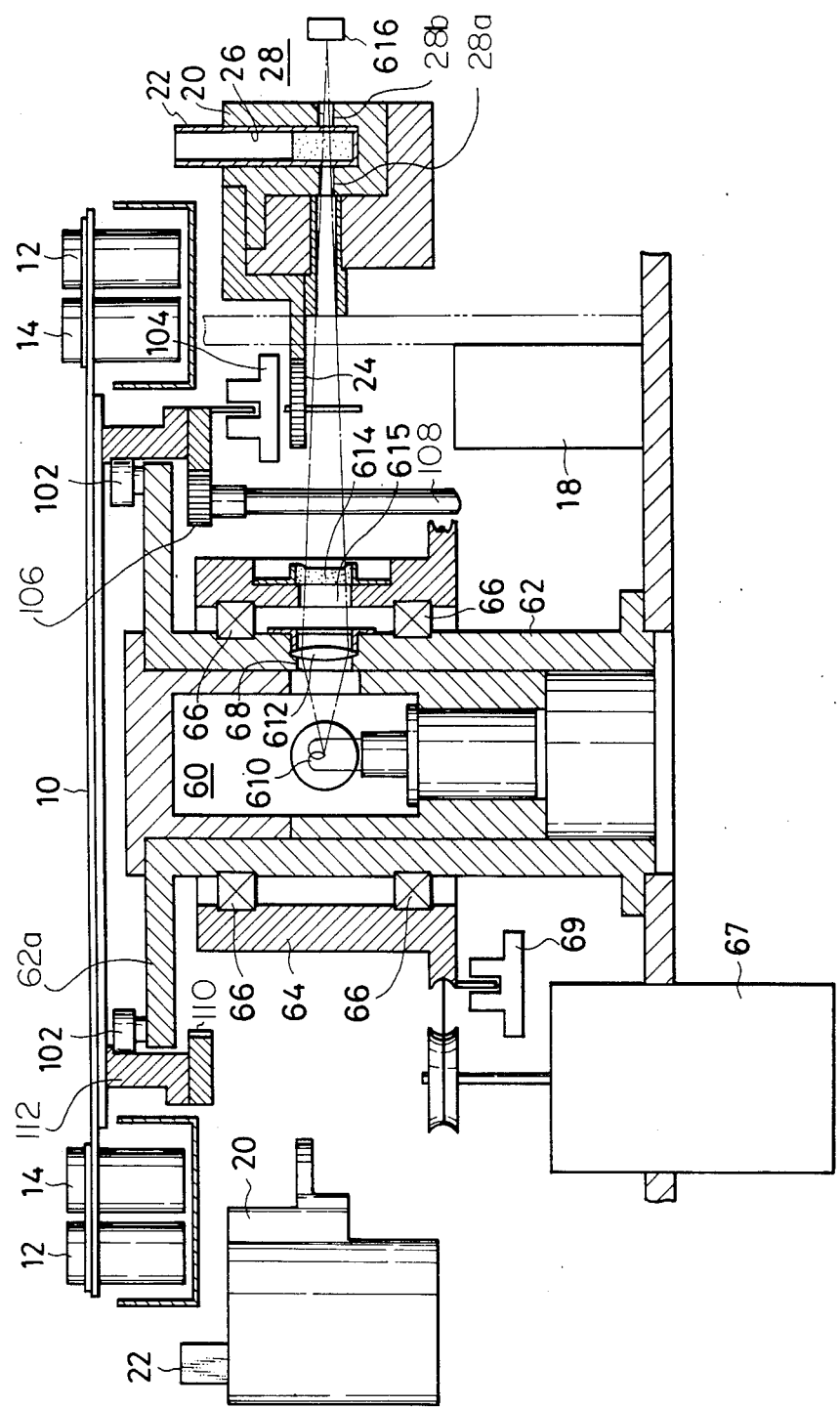
FIG. 2 is a cross-sectional view taken along the line II—II of FIG. 1.

Referring first to FIGS. 1 and 2, an automatic analysis apparatus constructed in accordance with a first preferred embodiment of the present invention is indicated by the reference character X. The main units of the analyzer X includes a sample table 10 rotatably disposed for rotation about a vertical axis. A plurality of sample containers 12 are arranged along an outer diameter in the top surface of the sample table 10, and each contain therein a sample to be examined such as blood serum or urine.

Also, a plurality of diluent containers 14 are laid on the sample table 10 along an inner diameter, internally of the sample containers 12, and each contain therein a diluent to be mixed with the sample so as to give a sample solution of a known concentration.

The sample table 10, as may best be shown in FIG. 2, is operatively connected to a drive means 18 which rotates the sample table 10 on a plurality of guide rollers 102 that are freely rotatably disposed on top of a flanged portion 62a of a stationary column 62; in a stepping manner to move the sample containers 12 successively to a predetermined sampling position, largely designated at "a", where an aliquot of sample is taken from the sample container 12 as will later be explained. This aliquot is mixed with a measured part or all of the diluent of known concentration in the diluent container 14 located radially internally of the sample container 12. The drive means 18 may be a pulse motor and may preferably has sensor means 104, to identify each sample container 12 as it is moved into the sampling position "a". The shaft 108 is drivingly connected to the drive means 18 which may be any known power transmission deviceable to rotate the shaft 108 in a stepping manner through a gearing or a transmission belt to rotate the internal gear wheel 110 and hence the sample table 10 through the pinion gear 106.

A reaction table 20 having at its top end a rimmed portion 29; said reaction table 20 is rotatably disposed and is mounted around the sample table 10, for rotation about the same axis as the table. A plurality of reaction vessels 22 are arranged along a circle in the top surface of the reaction table 20. The reaction table 20 is also operatively connected to a drive means 24 which rotates the reaction table 20 in a stepping manner to carry the reaction vessels 22 successively to a predetermined position, largely indicated at "c", where a sample and a diluent are mixed into the reaction vessel 22 to produce a sample solution. Likewise, the drive means 24 may be a pulse motor, which is run independently of the drive means 18, and may preferably include sensor means, not shown, to identify each reaction vessel 22 as it comes into the position "c".

On both sides of the sample table 10 are mounted a first and a second reagent table 30. Since the reagent tables 30 are similar in construction to each other, only the first reagent table 30 will be described to avoid unnecessary repetition. Accordingly, the description for the first reagent table 30 also refers to the second one. The first reagent table 30 carries on the top surface thereof a plurality of reagent containers 32 circumferentially arranged along the outside periphery of the table, each provided to contain therein a reagent selected for the particular analysis. The reagents are dispensed and mixed with the sample solutions in the reaction vessels 22 and the reactions taking place in them are monitored.

The first reagent table 30 is operatively connected to a drive means 34 which rotates the reagent table in a stepping manner to move the reagent containers 32 successively to a predetermined pickup position, largely indicated at "d", where a measured amount of reagent is taken from the vessel and dispensed into the proper reaction vessel 22. The drive means 34 may be a pulse motor and may preferably have sensor means, not shown, to identify each reagent container 32 as it is moved to the dispensing position "d".

In this particular embodiment, the operation of the first and second reagent tables 30 will be described as they are adapted to each carry a different group of reagents in their reagent containers 32. However, two or more kinds of reagents may be placed in an ordered array on the table for different analyses on a single run.

Adjacent to the reaction table 20 is provided a cleaning device 200 of any conventional design for automatic anlaysis apparatus at which every reaction vessel 22 dirtied in the previous operation is washed clean in six stages. In the first two steps, it is rinsed in detergent solution and in later stages washed with clean water. Preferably, at least one of the reaction vessels 22 being employed in the next round may be filled with water in order that a blank test may be carried out for the reactions taking place in the rest of the reaction vessels 22.

Figure 3:
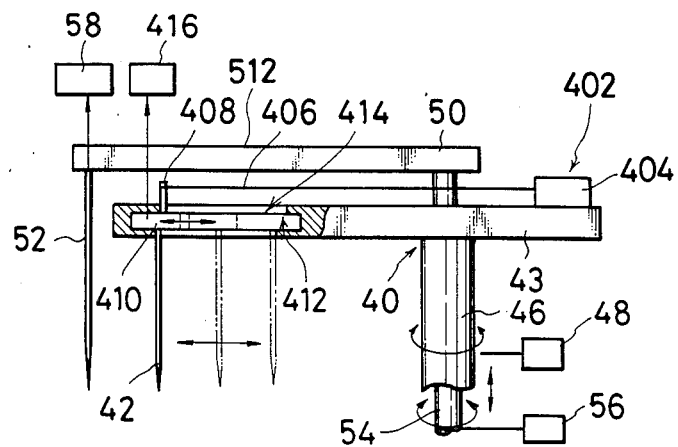
FIG. 3 is a cross-sectional view of a sampling mechanism integrated with a reagent dispensing device for the embodiment of FIG. 1.

A sample pipetting device, largely indicated at 40, is provided mounted between the sample table 10 and first reagent table 30. Referring to FIG. 3, the sample pipetting device 40 consists of a vertical rotatably disposed shaft 46, a horizontal sampling arm 43 pivotally disposed at a rear end thereof on the top end of the shaft 46, and a pipetting tube 42 fixed to the other end of the sampling arm 43.

The pipetting tube 42 is connected through a line, not shown, to a sampling pump 416 which causes the pipetting tube to suck up a measured amount of sample or diluent from the sample containers 12 or diluent containers 14. The pipetting tube 42 is also connected to a pump 76 for electrolytic analysis through a suitable changer which switches between the sampling pumps 416 and pump 76. The sampling pump 416 is connected to control means, not shown, to control the sucking and dispensing of the pipetting tube 42. Furthermore, sensor means of conventional art, not shown, is provided to monitor the suction of the pipetting tube 42 and send information to the control means so that the pipetting tube 42 can suck an accurately measured amount of sample or diluent with automated adjustment.

Preferably, the sampling pump 416 may be operated to cause the pipetting tube 42 to suck up the sample or diluent aliquot after some amount of water, with the interposition of air held inbetween enough to separate them, so that, after the pipetting tube has discharged the aliquot, the water is used to flush its inside. This flushing may preferably be done at a predetermined washing position, not shown, away from the foregoing operations positions "a" and "c".

The sample pipetting device 40 has drive means 48, which may be mounted at the vertical shaft 46, which rotates through the sampling arm 43 the pipetting tube 42 about the axis of the shaft 46 through an arc, as depicted in FIG. 1, between the operating and washing positions.

Furthermore, the drive means 48 is designed to move through the shaft 46 the sampling arm 43 vertically between an upper travelling position where the sampling arm 43 can be horizontally between the foreging positions and a lower operating position where the pipetting tube 42 is held just above the container or reaction vessel for suction or dispensation.

In this particular embodiment, the pipetting tube 42 is made to dispense the sucked amount of sample from the sample container 12 at position "a" or pick up a measured amount of diluent in the diluent container 14 located at position "b", just radially outwardly of the position "a". Moreover, a predetermined position for electrolytic analyses, not shown, may preferably be provided somewhere adjacent the sample table 10 within the reach of the sample pipetting device 40 where a required amount of sample from the sample containers 12 is collected and electrolytically tested through the pipetting tube 42 now connected to the pump 76.

Thus, the pipetting tube 42 has to be moved between at least three radially spaced points from the axis of rotation of the sampling arm 43; the furthest position where the pipetting tube 42 can reach the diluent container 14 at position "b", the middle position where it is rotated through an arc to cover the sample container 12 at position "a" and reaction vessel 22 at position "c", and the nearest point for the electrolytic and washing positions.

To this aim, according to this particular embodiment, the sample pipetting device may be constructed as follows as shown in FIG. 3. The sampling arm 43 has an axial hollow portion 412 extending through a forward end thereof. A pipette holder 410 is slidably disposed in the hollow portion 412 for axially sliding movement relative to the sampling arm 43 between three locations, determined to correspond to the foreging outermost, middle and nearest points with respect to the axis of the shaft 46. The pipetting tube 42 in turn is supported fixedly by the pipette holder 410.

The pipette holder 410 has a vertical pin 408 extending upward through a slit 414 formed in the top wall of the sampling arm 43. Control means 402 is provided mounted at a rear part of the sampling arm 43, which consists of a motor 404 and a power transmitting wire or cord 406 one end of which is wound around the shaft of the motor 404. The other end of the wire 406 is secured to the vertical pin 408. The operation of the control means 402 moves through the wire 406 the pipette holder 410 such that the pipetting tube 42 can selectively be shifted between the three points.

With this arrangement, the pipetting tube 42 can be rotated through an arc, with the arm in its upper travelling position, and moved radially to the desired sample container 12 at position "a" or sample container 12 at position "c", reaction vessel 22 at position "c", washing position or position for electrolytic analyses. When the pipetting tube 42 is set at such desired location, it is lowered to its lower operating position for suction, discharge or washing.

It may be preferable that the pipetting tube 42, while not in operation, is located at the washing position as its home position.

Mounted between the sample table 10 and each of the reagent tables 30 are a pair of first and second reagent pipetting devices 50, as shown in FIG. 1, which is operated to pick up a measured amount of reagent from the reagent container 32 located at position "d" and dispense it into the reaction vessel 22 as it is moved to a predetermined reaction position "e".

Since the first and second reagent pipetting devices 50 are substantially similar in construction to each other, except that the former is integrated in design with the sample pipetting device 40, only the first reagent pipetting device will be described to avoid unnecessary repetition. However, it should be understood that the description also refer to the other pipetting device.

Referring again FIG. 3, the reagent pipetting device 50 comprises a vertical rotatably disposed shaft 54, a horizontal reagent arm 512 fixedly supported at its rear end at a top part of the shaft, and a reagent pipetting tube 52 affixed to the other end of the reagent arm 512.

The reagent pipetting tube 52 is connected to a reagent a pump 58 which caused it to suck up a measured volume of reagent from the reagent container 32 located at position "d". Control means, not shown, may preferably be connected to the reagent pump 58 to control the suction and discharge of the reagent pipetting tube 52.

Furthermore, the reagent pipetting tube 52 may preferably have sensor means, not shown, to monitor its suction and send information to the control means so that the reagent pipetting tube 52 can suck an accurately measured amount of reagent with automated adjustement.

Also, as with the pipetting tub 42 of the sample pipetting device 40, the reagent pump 58, in operation, causes the reagent pipetting tube 52 to suck up the reagent after some amount of water, with the interposition of air held in between enough to prevent direct contact between the reagent and water, so that, after the sucked reagent has been dispensed, the water is forced out to flush the inside of the reagent pipetting tube 52 clean. Preferably, this cleaning operation may be effected at a predetermined position, not shown, away from the positions "d" and "e".

The reagent pipetting device 50 has drive means 56, which may be mounted at the shaft 54, to rotate the reagent pipetting tube 52 about the axis of the shaft through the reagent arm 512 between positions "d" and "e" and the foregoing washing position. The drive means 56 also moves the shaft 54 vertically between an upper travelling position where the reagent arm 512 is rotated between the operating and washing positions and a lower operating position where the reagent pipetting tube 52 picks up the reagent from the vessel at position "d", dispenses it into the reaction vessel 22 at position "e", or is washed at the washing position. Likewise, it is preferable that the reagent pipetting tube 52 is located at the washing position as its home position while not in operation.

Although the first reagent pipetting device 50 is integrated with the sample pipetting device in this particular embodiment, as depicted in FIG. 3, it should be understood that the drive means 56 is able to drive the reagent pipetting device 50 regardless of the operation of the drive means 48 for the sample pipetting device. Furthermore, the reagent arm 512 of the reagent pipetting device 50 is made long enough to has its reagent pipetting tube 52 stand out of the way of the pipetting tube 42 even when the sampling arm 43 of the sample pipetting device 40 is at its outermost position.

Referring back to FIG. 1, the operation of the sample pipetting device 40 is timed with the rotation of the sample table 10 and reaction table 20 such that, when the sample pipetting device 40 has completed the discharge of the mixture of measured amounts of sample and diluent taken from the sample container 12 and diluent container 14 at positions "a" and "b", respectively, into the reaction vessel 22 now moved to position "c", the reaction table 20 is rotated counterclockwise (in the drawing) to bring that reaction vessel 22 one pitch to position "e".

Since the operation of the first reagent pipetting device 50 is also timed with the rotation of the reaction table 20 and first reagent table 30, the reagent picked up by the reagent pipetting device 50 from the reagent container 32 at position "d" is discharged into the reaction vessel 22 when it has just come into position "e".

The timed operation of the sample pipetting device 40 and reagent pipetting device 50, along with the rotation of the sample table 10, reaction table 20 and reagent tables 30, may preferably be controlled by a properly designed microcomputer program in conjunction with suitable sensing means for identifying each sample or chemical container on the tables.

In addition, the sampling pump 416 and reagent pump 58 for the sample pipetting device 40 and reagent pipetting device 50 each may employ a microsyringe and driven through a pulley by a pulse motor which controls the amount of suction by the pipette as a function of the number of pulses generated by the motor.

To allow the sample to properly react with the reagent in the reaction vessel 22, its contents have to be thoroughly blended. This is done by agitator means 510 provided on each reagent pipetting device 50. Since the agitator means 510 for the both reagent pipetting device 50 are substantially similar in construction, only one of them will be described. Needless to say, the description should refer to the other agitator means.

Figure 4:
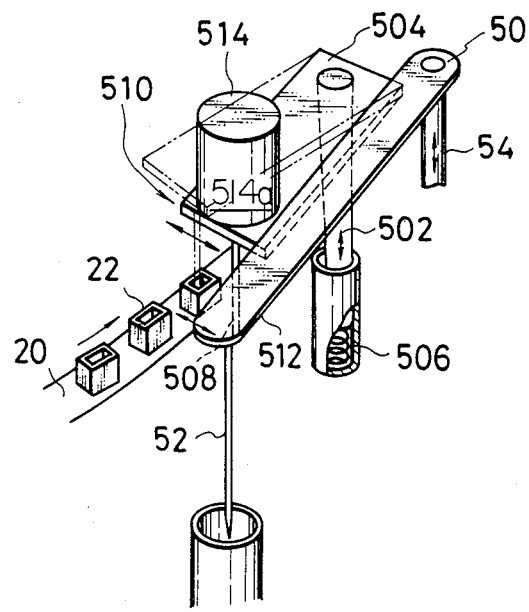
FIG. 4 is a perspective view of the sampling mechanism with an agitator for the embodiment of FIG. 1.

Referring then to FIG. 4, the agitator means 510 consists of a vertical column 502 rotatably disposed for rotation about its own axis, a horizontal arm 504 fixedly supported at its rear end at a top portion of the column, a coil spring 506 fitted about a lower portion of the column 50 in such a manner to urge the column in the upward direction, a stirring rod 508 secured to a forward end of the horizontal arm 504, and a motor mounted on top of the arm and having its drive shaft coupled to the upper end of the stirring rod 508 in such a manner that the torque of the motor 514 is transmitted to the stirring rod 50 causing a vibratory motion in it. A spring, not shown, is provided in the column 502 to urge the horizontal arm 504 in the counterclockwise direction to a washing position which will later be described in detail.

The agitator means 510 is integrated with the reagent pipetting device 50 in such a manner that the movement of the latter determines the position of the former physically. When the reagent arm 512 of the reagent pipetting device 50 in its upper travelling position is rotated horizontally to bring the reagent pipetting tube 52 to the current reaction vessel 22 at position "e", the horizontal arm 504, which is located slightly below the reagent arm 512, is also forced to move against the spring in the same direction into a stirring position where the rod 508 stands above the reaction vessel 22 just ahead of the current reaction vessel.

In other words, the reaction vessel 22 whose contents are now being stirred by the agitator means 510 is the one into which the reagent pipetting device 50 has just dispensed the reagent in the previous dispensing operation while at position "e".

When the reagent arm 512 is lowered bringing its reagent pipetting tube 52 into the lower operating position for discharge into the reaction vessel 22 at position "e", the horizontal arm 504, pressed by the reagent arm 512, is also moved down against the spring 506 to lower the stirring rod 508 into the reaction vessel 22 next to position "e" where the motor 514 is energized to cause the rod to vibrate mixing the reaction vessel contents into a homogenous state.

When the reagent arm 512 is raised after the completion of the discharge, the horizontal arm 504, now released, is restored to its original upper position, forced by the action of the spring 506. When the reagent arm 512 is rotated counterclockwise to the washing position, the horizontal arm 504 is released and forced by the action of the spring into its washing position where the rod is rinsed and wiped dry by a suitable cleaning device of known art.

Referring to FIG. 2, a photometer system 60 is provided for monitoring the reaction of a diluted sample solution to known concentration, mixed with a reagent in the reaction vessel 22 for a period of time in biochemical analysis.

The photometer system 60 consists of a source of 610 mounted in a cylindrical column 62 of light-tight structure provided in fixed position at the center of the sample table 10, a filter frame 64 rotatably disposed about the cylindrical column 62 through bearings 66 for rotation about the axis of the cylindrical column 62, and drive means 67 to rotate the filter frame 64 through a conventional belt or gear mechanism. The light source 610 produces an optical beam that traverses the cylindrical column 62 and filter frame 64 to pass through a reaction vessel 22 and the contents therein to be sensed by a photodetector 616.

For the beam from the light source 610 to reach the reaction vessel 22, a plurality of circumferential apertures 68 are defined in the wall of the cylindrical column 62, with a lens 612 fitted in each aperture 68. The focal length of each condensing lens 612 must be selected to cause the beam to focus at the photodetector 616. Likewise, a plurality of holes 615 are defined in the wall of the filter frame 4, with a filter 614 fitted in each hole 615.

The pair of holes 28 at substantially diametrically opposite points in the walls of the receptacle 26 where the reaction vessel 22 is exposed to the beam from the light source 610 that goes through the hole 615 to enter the receptacle 26 and hence the vessel 22 through the nearer hole 28a and leave it through the remote holes 28b to be sensed by the photo detector 616 for photometric analysis.

The photodetector 616 may preferably be provided at each of fixed locations about the reaction table 20. Furthermore, the reaction vessels 22 may preferably be made of hard glass or a chemical resistant plastic material with adequate transparency and shaped to a square cross section for increased sensitivity of a photodetector 616 employed.

The apertures 68 may be in the same number as the holes 615 in the filter frame 64 and the photodetectors 616 (8 pieces in this particular embodiment as shown in FIG. 1, and provided in the stationary column 62 at such locations that the reaction vessels 22 are radiated after they pass the reaction position near the second reagent table 30.

Furthermore, the filters 614 may preferably be different in property from on-e another such that the optical beam from the light source 610 is converted to a range of different wavelengths. Means 69 are provided to identify the filters 614 as the filter frame 64 is rotated at constant speed by the drive means 67. With this arrangement, a photodetector 616 can, in conjunction with the means 69, monitor the contents of the reaction vessels 22 at different wavelengths.

The output of each photodetector 616 may be connected to a data recorder which processes the results of their readings.

Also, a fluorescent penetrant inspector 80 is provided for EIA analysis of samples in beaded solid phase. The inspector 80 includes a source of light, not shown, which directs an optical beam to the reaction vessel 22 through a filter, not shown, that converts the light to a wavelength of 255 nm to be passed through the contents of the reaction vessel 22 via quartz fibers, an interference filter to receive the rays at 365 nm reflected through the reaction vessel 22 in a direction perpendicular to the incident light, a photocell, a detection circuit, a control board, and an inspector control. Since the operation of the inspector 80 is well known, description is omitted in this specification.

The pump means 76 for electrolytic analyses may comprise a first pump for transferring standard liquid, a second pump for moving a sample, sucked up by the pipetting tube 42 of the sample pipetting device 40, to a flow cell, and a third pump for transferring compared liquid.

Means is provided to control the temperature of the reaction vessels 22 by circulating through a line inbedded in the reaction table 20 water heated to a maintained temperature level selected for the intended analysis.

Also, means is provided to keep the reagent container 32 at both first and second reagent tables 30 at approximately 10° C. by circulating cooled water.

The functions of the automatic analysis apparatus X according to this invention may preferably be connected to a microcomputer so that the operation for various analyses can be controlled by a program loaded into the hardisk.

In biochemical analysis, a measured amount of sample from the sample container 12 located at position "a" is sucked up by the pipetting tube 42 of the sample pipetting device 40 and transferred into the reaction vessel 22 at position "c", and then mixed with a measured amount of first reagent by the reagent pipetting tube 52 of the first reagent pipetting device 50 taken from the reagent container 32 at position "d" as that reaction vessel 22 is rotated one pitch to position "e", with the mixture being stirred to a homogenous state by the agitator means 510. Then, the reaction table 20 is rotated to bring the reaction vessel 22 to second position "e" where a measured amount of second reagent from the reagent container 32 at position "d" on the second reagent table 30 is dispensed into it by the second reagent pipetting device 50, with the mixture also being agitated to a uniform state by the agitator means 510. While the reaction vessel 22 is rotated further, the eight photodetectors 616 monitors the progress of the reaction taking place in it for a continued period of time, and the results of the successive readings may be analyzed by colorimetry.

In this case, the diluent containers 14 may be used to contain blank, standard or control liquid, or emergency sample.

Furthermore, each of the reagent tables 30 may contain two or more reagents in the number of reagent containers 32, each marked with an identification code.

In immunological analysis, a measured amount of sample and diluent are taken from the sample container 12 and diluent container 14 located at positions "a" and "b", respectively, into the cuvette at position "c" by the sample pipetting device 40 to prepare a sample solution of known desnity. When the reaction vessel 22 is rotated to position "c", the reagent pipetting device 50 dispenses a measured amount of first reagent from the reagent container 32 at position "d" into it, with the mixture being stirred by the agitator means 510. Then, the reaction taking place in the reaction vessel 22 is "monitored in substantially the same manner as in biochemical analysis.

In electrolytic analysis, an aliquot of sample is sucked up from the sample container 12 at position "a" by the sample pipetting device 40 and discharged into a container located at the electrolytic analysis position. The sample aliquot is then transferred to an analysis station 72, not shown.

In EIA analysis of sampled in beaded solid phase, a larger container containing beads may be employed. The reaction table 70 may be superceded by a special tray for EIA analyses. The sample and reagent used are also treated for EIA analysis by known method.

Referring now FIGS. 5 through 7, a second preferred embodiment of the present invention will be described.

Figure 5:
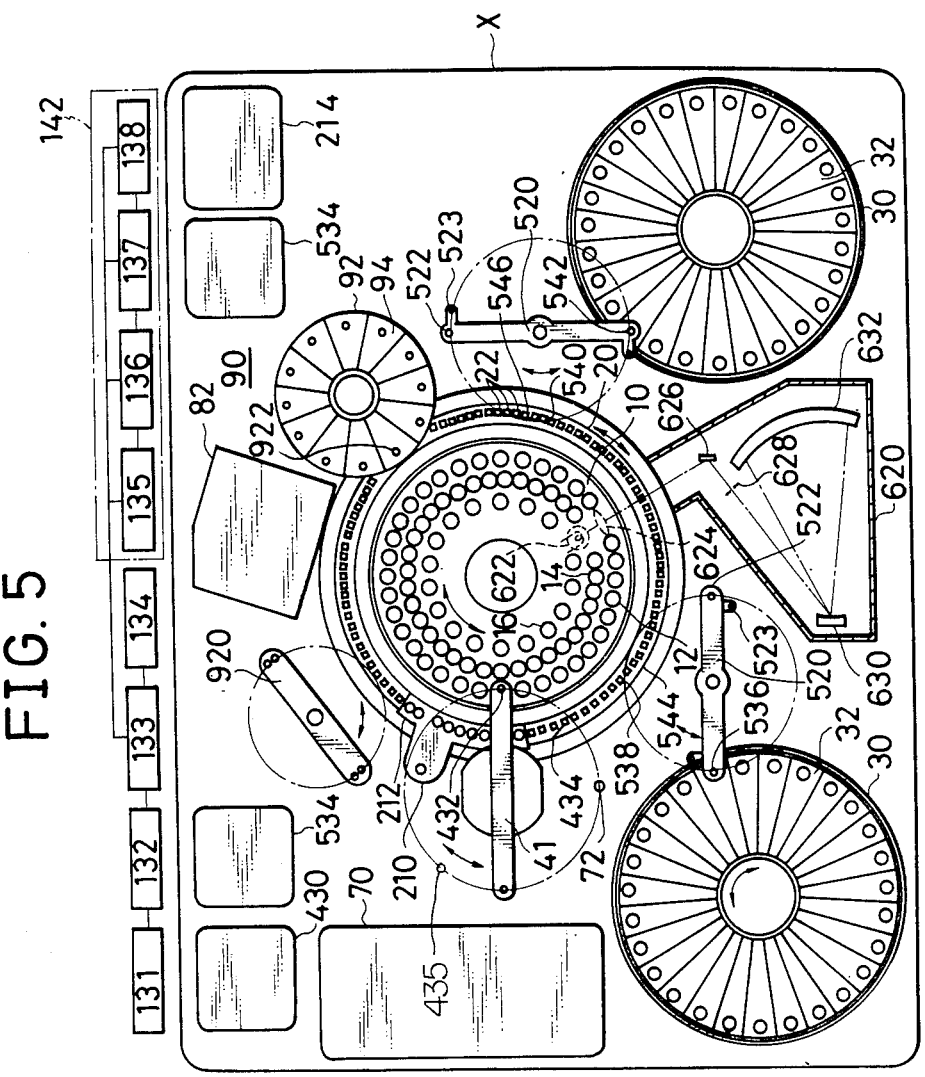
FIG. 5 is a plan view of a second preferred embodiment of the automatic analysis apparatus according to the present invention.
Figure 6:
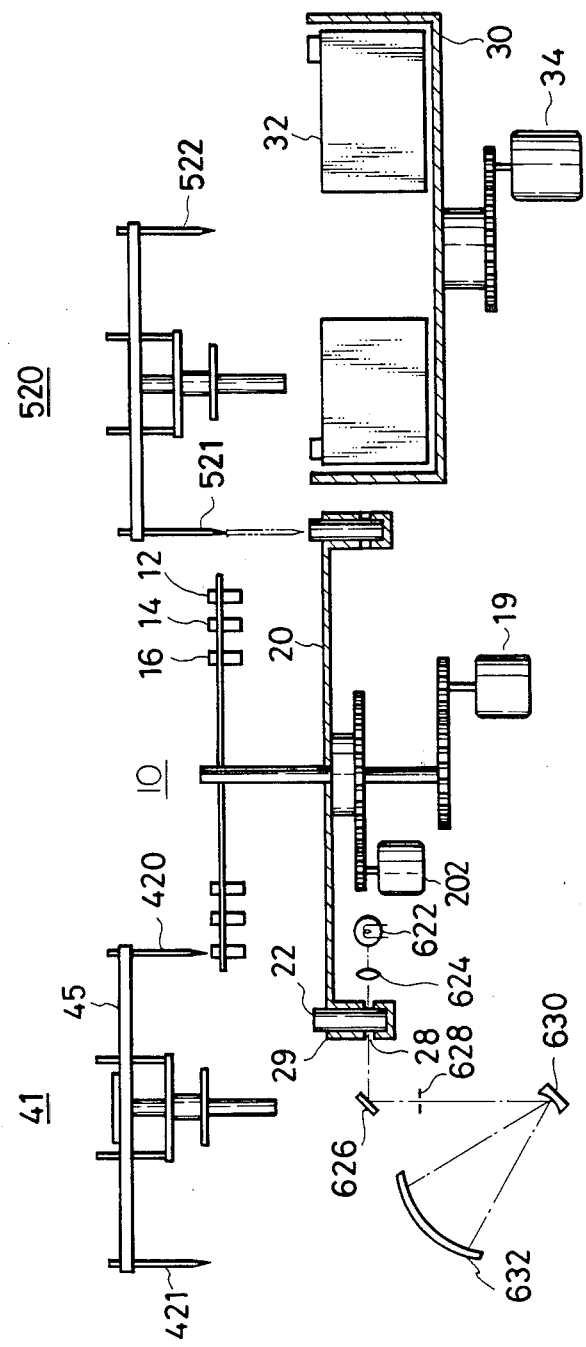
FIG. 6 is a cross-sectional view of the analyzer shown in FIG. 5.

In FIGS. 5 and 6, an automatic analysis apparatus X includes a turret-like sample table 10 which is substantially similar in design to the previous embodiment except that there is added a plurality of containers 16 each containing therein an emergency sample, circumferentially arranged internally of the diluent containers 14. The sample table 10 is driven by drive means 19 in a stepping manner brings the sample containers 12 successively to a predetermined sampling position, indicated at 432 where a measured amount of sample is taken from the sample container 12 as will later be described.

While each sample container 12 is at position 432, a measured amount of diluent may be taken from the diluent container 14 now located radially internally of the sample container 12 to provide a sample solution of known density.

A reaction table 20 is rctatably disposed around the sample table 10 and carries thereon a plurality of circumferentially arranged reaction vessels 22, just as in the first embodiment. Thereaction table 20 is rotated by drive means 202 in a stepping manner to move the reaction vessels 22 successively to a predetermined discharge position, designated at 434, where the aliquot of sample taken from the cup at position 432 is discharged into the reaction vessel 22.

Similarly, a first and a second reagent table 30 are provided, each with a plurality of reagent containers 32 circumferentially arranged along their periphery. Each of the reagent containers 32 on the first reagent table contains therein a first reagent while the reagent containers on the second reagent table each contain a second reagent. The reagent tables 30 are individually rotated by a separate drive means 34 to rotate their reagent container 32 in an indexing manner to a predetermined position 536 (in the case of the first reagent table) or 542 (in the second reagent table) at which a measured amount of reagent is picked up, moved over to the reaction table 20, and discharged into the reaction vessel 22 that is just moved to position 538 (for the first reagent) or 540 (for the second reagent).

The sample table 10, reaction table 20, and both reagent tables 30 are each provided with sensor means, not shown, of conventional art to identify each of their containers as they are rotated into the proper operating position for sampling, discharging or dispensing, so that the progress of the reaction for a particular sample in the cuvette can be followed up.

Figure 7:
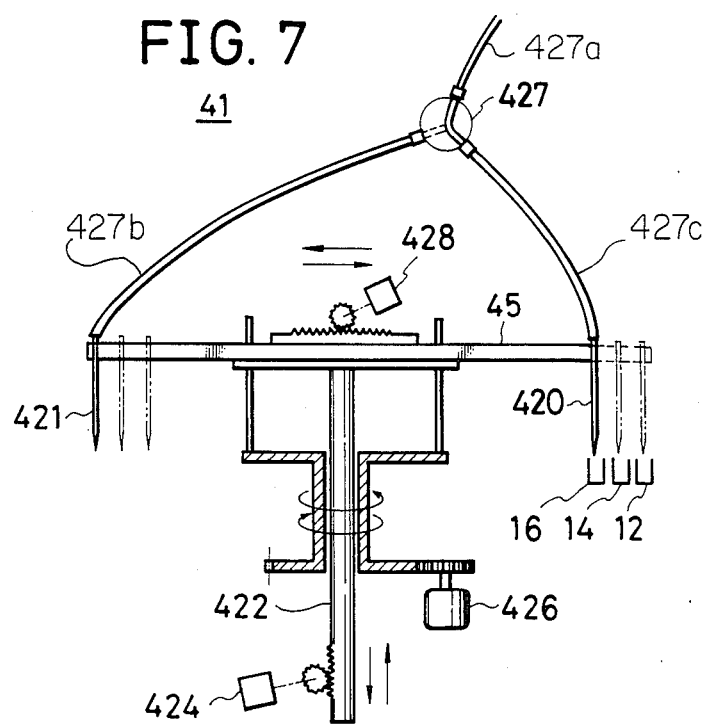
FIG. 7 is a schematic view of a sampling mechanism for the second embodiment.

Referring now to FIG. 7, a sample pipetting device 41 is provided adjacent to the sample table 10, which is substantially similar in junction and operation to the sampling device of the first preferred embodiment, except that it has a pair of sample pipetting tubes 420 and 421 fixedly mounted on both ends of a horizontally slidably disposed pipette holder 45 for shifting the sample pipetting tubes 420, 421 between three horizontally spaced positions. This sliding movement of the pipette holder 45 may be effected by a pinion and rack mechanism 428, with suitable conventional means, not shown, to lock the pipette holder 45 at each of the three positions as desired.

The pipette holder 45 is fixedly supported at its center on the top of a vertical column 422 pivotally disposed for rotation about its own axis. Operatively connected to the vertical column 422 is drive means 426 which rotates the pipette holder 45 about the vertical column 422. In addition, the vertical column 422 is vertically slidably disposed and may be moved vertically by a rack and pinion mechanism 424 between an upper travelling position where the pipette holder 45 can be rotated to locate its sample pipetting tubes 420 and 421 at their operating position and a lower operating position where the sample pipetting tube may be lowered into the container at its proper position for sampling or dispensing.

The sample pipetting tube 420 and 421 is connected to a sampling pump 430 (FIG. 5) through an electromagnetic control valve 427 which connects the sampling pump 430 to either of the sample pipetting tubes to control the suction and discharge of the sample pipetting tube.

In actual practice, the sample pipetting tube may be made to aspirate an amount of water first, and then the sample aliquot, with the interposition of some air enough to prevent direct contact between them, so that the sucked water, after the dispensation of the aliquot into the reaction vessel 22, is forced out to flush the inside of the sample pipetting tube. Preferably, this flushing may be carried out at a position diametrically opposite to position 432, to which the sample pipetting tube may be automatically rotated through 180° after each dispensation.

This design enables the sample pipetting tubes 420 and 421 to be employed in an alternate manner. Rotation of the current sample pipetting tube, after discharge of its sample portion, to the flushing position brings the other sample pipetting tube to position 432. While this pipetting tube is used for sampling operation, the first pipetting tube is cleaned inside so that it is prepared ready for the next sampling operation, thereby reducing operating time.

With this arrangement, in operation, the one sample pipetting tube 420 in its lower operating position may be set to the retracted position to suck a measured amount of sample from the sample container 12 at position 432 or the outermost position to pickup an aliquot from the emergency container 16 at the position radially externally of sample pipetting tube 420. After the suction, the sample pipetting tube 420 is raised to the upper travelling position and rotated to the reaction vessel 22 at position 434 where the sample pipetting tube may be lowered to the operating position to dispense the sucked aliquot into the reaction vessel 22. The sample pipetting tube 420 may be raised, rotated back to the original position, and, after having been set to the middle position, lowered into the diluent container 14 to suck a measured amount of diluent to be mixed iwth the sample aliquot in the reaction vessel 22 at position 434.

On the first and second reagent tables 30, respectively, are provided a pair of first and second reagent containers 32 on both sides of the sample table 10, which provide a measured amount of reagent, selected for the analysis being conducted, to the reaction vessel 22 at a predetermined position 538 (in the case of the first reagent pipetting tube) or 540 (in the case of the second reagent pipetting tube).

Since the reagent pipetting devices 520 are substantially similar in construction to each other, the first reagent pipetting device only will be described. However, it should be understood that the description refers to the other reagent pipetting device.

Figure 8:
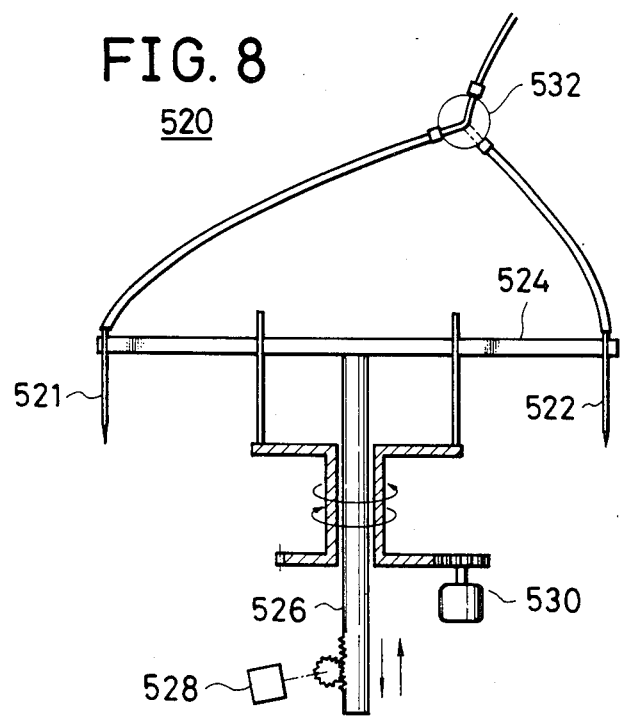
FIG. 8 is a schematic view of a reagent dispensing device for the second embodiment.
Figure 9:
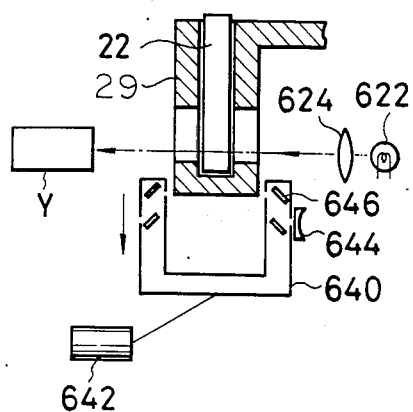
FIGS. 9 and 10 is respectively a schematic view of a photometer system for the second embodiment, showing a different operating position.

Referring to FIG. 8, the reagent pipetting device 520 consists of a vertical shaft 526 rotatably disposed for rotation about its axis, a pipette holder 524 fixedly supported at its midpoint on the top of the shaft 526, and a pair of reagjent pipetting tubes 521 and 522 fixedly mounted at both ends of the pipette holder 524.

The shaft 526 is rotated by drive means 530 to turn the pipette holder 524 the reagent pipetting tubes 521 and 522 for a purpose as will later be described. Also, the shaft 526 is moved vertically by a rack and pinion mechanism 528 to move the pipettes between an upper travelling position where the pipette holder 524 can be rotated by the drive means 530 and a lower operating position where the reagent pipetting tubes can suck up an aliquot of reagent from the vessel located at 536 or, in the case of the second pipetting tube, 542, or discharge the sucked reagent aliquot into the cuvette that has just been moved to a predetermined dispensation position 538 or, in the case of the second pipetting tube, 540.

The reagent pipetting tubes 521 and 522 are connected to a reagent pump 534 via an electromagnetic valve 532 which switches connection to the pump 534 between the reagent pipetting tubes. Thereagent pump 534 controls the suction and dispensation of the reagent pipetting tubes. Preferably, sensor means, not shown, may be attached to each reagent pipetting tube to detect the lowering of the reagent pipetting tube into the reagent vessel for suction and send information to the mechanism 528 which in turns acts to prevent the reagent pipetting tube from being submerged too deep into the reagnet.

As with the sample pipetting device 41, it is so designed that the pipetting tube 42 in operation sucks a proper amount of water first and then sucks the reagent aliquot, with the interposition of some air. The sucked water is used to flush the pipetting tube insdie. This flushing may preferably be done at a predetermined cleaning position diametrically opposite to position 536 or, in the case of the second pipetting tube, 542, so that the pipetting tubes is used in an alternate manner.

With the above-mentioned arrangement, in operation, the reagent pipetting device 520 in their upper travelling position is rotated and lowered to a lower operating position at the proper container at position 536 or 540 (for a second reagent) to suck up a measured amount of reagent from the vessel. Then, the pipette holder 524 is raised again and rotated to the reaction vessle 22 that has just been rotated to position 538 or 548 (for a second reagent), and lowered to position 538 or 548 (for the second pipetter), and lowered to bring the proper reagent pipetting devices 521 or 522 into the reaction vessel 22 to dispense the sucked reagent to mix the sample in it.

To blend the mixture in the reaction vessel 22 uniformly, agitator means 523 may preferably be provided attached to each of the reagent pipetting tubes 521 and 522, which is operated after each dispensing operation by the pipetting tube. The agitator means may comprise a nozzle, not shown, and an air pump, not shown, operatively connected to the nozzle through a line and adapted to supply air thereto when the nozzle is inserted into a reaction vessel 22. The distance between each pipetting tube and its nozzle may be such that the latter operates at position 544 or 546 two steps ahead of the dispensation position 538 or 540.

The sample table 10, reaction table 20, and both reagent tables 30 are operated in a timed relationship with the sample pipetting devce 41 and both reagent pipetting devices 520 so that the mixing of a sample or emergency sample, with or without a diluent, with a first and a second reagent in a particular reaction vessel 22 to produce the desired reaction to be monitored is controlled.

Preferably, their operation may be governed to conduct a particular analysis by a program in a microcomputer 133 with a data processor 142 including a CPU 135 for processing the analysis results with a disk unit 137 for storing the data, and a CRT display 136 or a printer 138 for outputing the data (FIG. 5). The microcomputer 133 is connected to a power source through a power circuit 133.

Referring again to FIG. 5, a cleaning station 210 is provided, mounted adjacent to the sample table 10, for washing reaction vessels 22. When the reaction vessels 22, after the reaction taking place in them have been measured, are rotated to position 212, they are washed in detergent supplied from a detergent pump 214 at the cleaning station 210. The cleaning may preferably be done in eight steps including washing with an alkali and acid cleaning agent.

Also, a photometer system 620 is provided for biochemical analysis of samples. It is so designed that the photometer system 620 measures progressively the changes in light absorbance of samples in reaction vessels 22 after they have been mixed with a reagent, so that the progress of the reactions taking place in them is monitored as the reaction vessels 22 are rotated in the reaction table 20. Referring further to FIGS. 5 and 6, the system 620 comprises a source of light 622 which produces an optical beam to traverse a lens 624 to pass through a reaction vessel 22. The optical beam leaving the reaction vessel is reflected by a reflector 626 to go through a slit 628 to a spherical diffraction grating 630 which disperses the beam to be sensed by an optical sensor 632 such as a photodiode capable of sensing a wide range of wavelengths. The wavelengths sensed in the dispersed optical beams are converted by an analog-to-digital converter to an electrical signal to be computed to determine the density of the liquid in the reaction vessels.

Figure 10:
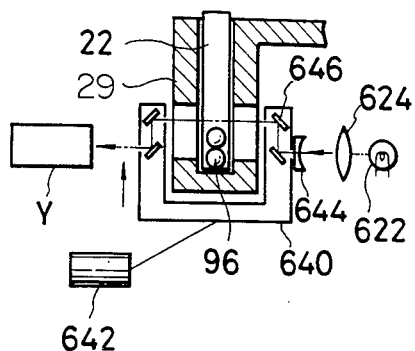

Each reaction vessel 22 has a pair of diametrically opposed slits 28 opened in its receptacle 29, as may best be depicted in FIG. 10, through which the beam from the light source 622 is passed through its contents for scanning.

In biochemical analysis where a sample requires mixing of two or more reagents from the reagent table 30, they are arranged in a required number of reagent containers 32 arranged in ordered sequence on the table. In this case, the reagent table 30 may be controlled to rotate back one step after every preceding reagent is dispensed so that the reagent pipetting tubes 521, 522 discharges the subsequent reagent at the same reagent dispensing position 538 or 540.

A sampling position for electrolytic analysis, designated at position 72, may preferably be located on the diameter of rotation of the sample pipetting device 41 in the retracted position of its arm 45. In electrolytic analysis, which may be carried out simultaneously with biochemical analysis, a container may be placed at position 72 to receive part of a sample through the sample pipetting device 41, and transported mechanically or manually to a test station 70 where the sample is electrolytically measured (FIG. 5). The station 70 may preferably be connected to the data processor 134 which processes electrolytical readings.

Figure 11:
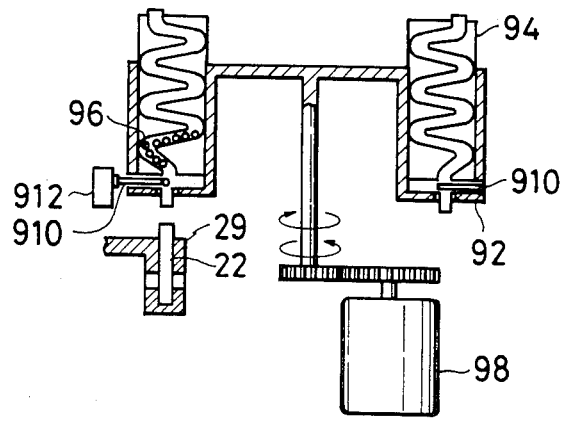
FIG. 11 is a schematic view of a bead dispensing device for the second embodiment.

Also, provision may be made for EIA analysis means 90 of samples in bead solid phase. Referring to FIGS. 5 and 11, a bead table 92 is located adjacent to the reaction table 20, which consists of a plurality of bead stockers 94 circumferentially arranged in the bead table 92, drive means 98 which rotates the bead table 92 in a stepping manner to move the stockers 94 successively to a predetermined feed position 922 where beads 96 are into the reaction vessels 22 as they are rotated to this position, and a lever 910 which is actuated by an electromagnetic solenoid 912.

A bead disposal device 90 is mounted at a proper point along the reaction table 20 from the bead table 92, which removes the beads 96 from the reaction vessels 22 as they are rotated, as the completion of the measurement, to a predetermined position, not shown, where the beads are removed from the reaction vessel 22. The device 920 may be composed of a suction nozzle for collecting beads by suction, lifting means to move the nozzle into the reaction vessel, and drive means to rotate the nozzle to the bead disposal position.

In a more preferred embodiment, optical beam transmitting means is provided which includes a movable frame 640 adapted to carry thereon said reaction vessels 22 and movably disposed for vertical movement relative to said reaction vessels 22 between an upper position for EIA analysis of samples in beam solid phase and a lower position for biochemical analysis. The movable frame 640 may preferably be drivingly connected to drive means 642 which moves the frame 640 between its upper and lower positions. In the upper position, the optical beam from the light source 622 traverses the reaction vessel 22 to be scanned through a straight horizontal path to be scanned by the optical sensor Y. On the other hand, in the lower position of the frame, the optical beam is guided to pass through an optical system composed of a lens 644 for focal adjustment and four reflectors 646, arranged at each monitoring location in the frame 640, such that the optical beam is allowed to traverse the reaction vessel 22, without being interrupted by the beads lying in the lower part of the reaction vessel 22, to be sensed by the optical sensor Y. Furthermore, this arrangement can provide for measuring with small amounts of sample is reaction vessels.

In addition, located between the bead table 92 and bead disposal device 920 is a fluorescence analyzer 82 which measures the density of drugs contained in blood. The procedure for fluorescence analysis using analyzer 82 is substantially similar to biochemical analysis, except that the rotation of the reaction table 20 must be arrested during operation.

In operation the sample in a vessel 22 is allowed to excite by optical beams directed through an intermediate filter which may produce a wavelength of 485 nm. The light leaving the sample is passed through a second interference filter, which may be a type capable of producing 525 nm, to be sensed by an optical sensory. The analyzer 920 may preferably be connected to a computing system which computes readings amplified and converted in digital form to determine the density of drugs contained in the sample.

Furthermore, a temperature control system 131 may preferably be provided which controls the temperature of the reaction vessels 22 at a constant level.

Figure 12:
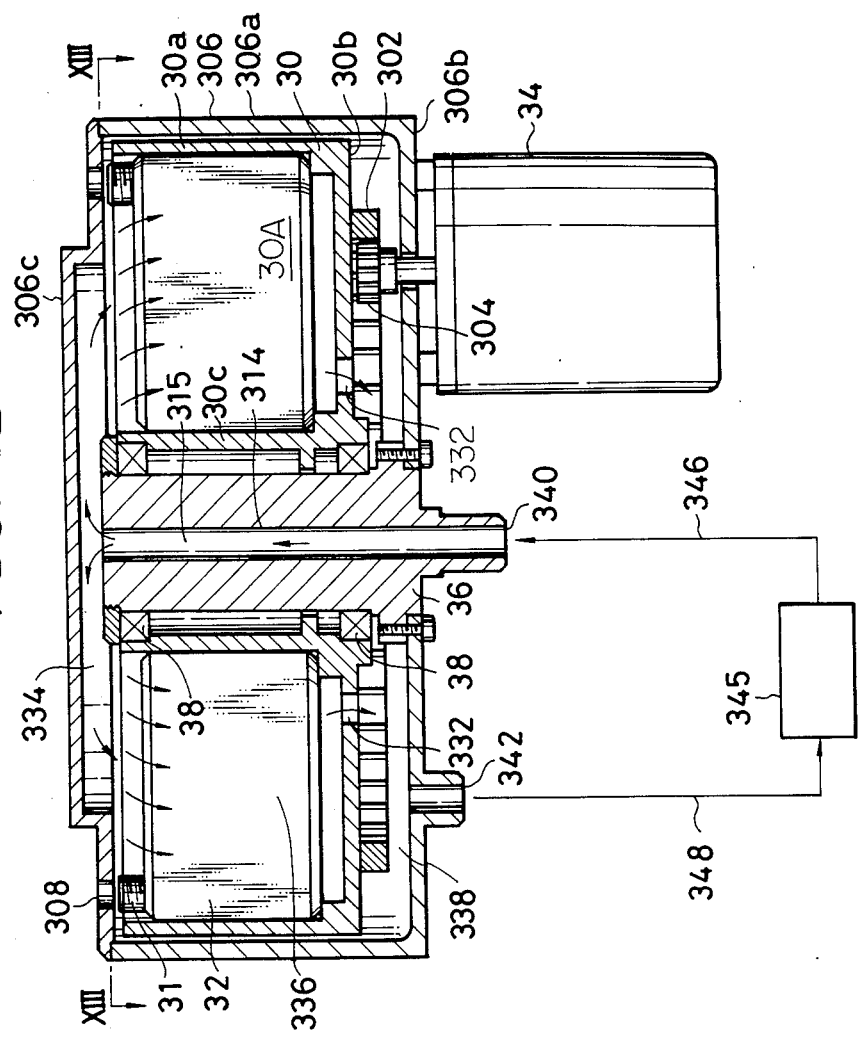
FIG. 12 is a cross-section view of a cooling system for the reagent table of the automatic analysis apparatus according to the present invention.
Figure 13:
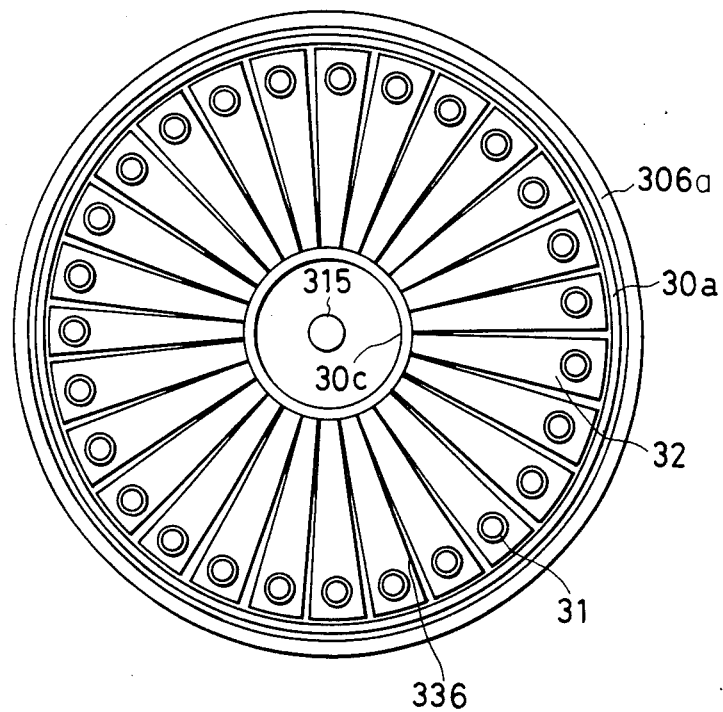
FIG. 13 is a view taken along the line XIII—XIII of FIG. 12.
Figure 14:
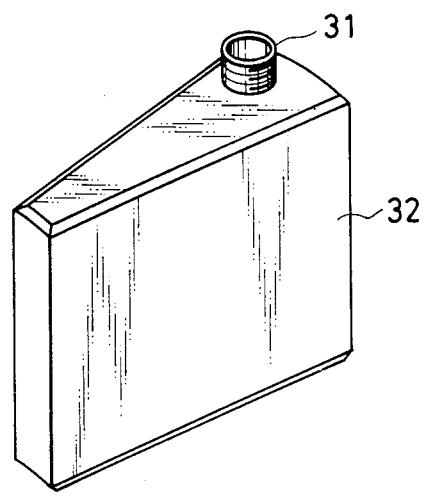
FIG. 14 is a perspective view of the reagent container.

Referring further to FIGS. 12 through 14, means 345 for cooling the temperature of the reagent containers 32 may preferably be provided in each of the first and second reagent tables 30. Since the both temperature cooling means are substantially similar in construction to each other, the one for the first reagent table 30 will be described. Thus, it should be understood that the description also refers to the other control means.

The reagent table 30 is supported by a fixed vertical column 36 in the center having an axial hollow portion 314. Also, the reagent table 30 includes a circular side plate 30a, a bottom plate 30b, and an inner plate 30c. The side plates 30a and 30c and bottom plate 30b form together a toroidal tray, generally designated at 30A, rotatably disposed on the column 36 through vertically spaced bearings 38 and rotated by the drive means 34 through its driving gear 304 that is in turn engaged with an internal gear 302 affixed to the underside of the bottom plate 30b.

The plurality of reagent containers 32 may preferably be shaped in cross section like a uniform sector of a circle, as depicted in FIG. 14, with an opening 31 at their top for sampling by the reagent pipetting tubes 521, 522, and arranged in a radial patter, as shown in FIG. 13, between the side plates 30a and 30c of the toroidal tray, with a gap 336 between the reagent containers 32 for proper ventilation.

The toroidal tray is enclosed by an outer housing 306 composed of a side plate 306a, a bottom plate 306b, and a top cover 306c, as may best shown in FIG. 12, with the bottom plate 306b secured to the column 36. The top cover 306c is levelled high enough above the top of the vessels 32 to provide a space 334 beneath the cover. Also, the top cover 306c is provided along its periphery with a plurality of apertures 308 at locations opposite the openings 31 of the reagent containers 32 to permit the insertion of the reagent pipetting tube 521, 522 for pipetting operation;

Furthermore, the bottom 30b of the toroidal tray 30A may preferably raised from bottom plate 306b to provide a space 338 below the tray. In addition, a number of throughholes 332 are defined through the bottom plate 30b.

The cooling means 345 may be any suitable type of known design capable of generating cooled air, which consists of a supply line 346 and a return line 348. The supply line 346 is connected to an inlet port 340 defined in the hollow portion 314 of the column 36 at its lower part to supply the toroidal tray 30A with cooled air through an axial message 315 defined in the hollow portion 314.

The return line 348 is connected to a single vent hole 342 formed in the bottom plate 306b.

With the above arrangement, the cooled air from the cooling means 345 can be circulated in the toroidal tray 30A, through the passage 315, space 334 between the top cover 306c and vessels 32, gaps 336 between the vessels, throughholes 332 in the bottom plate 30b, and space 338 beneath the plate 30b before returning to the means 345 through the return line 348.

The cooling means 345 may preferably be connected to a temperature control, not shown, to provide required temperature control depending on the type of the reagent used. This design can not only cools the liquid in the reagent containers 32 but also optimize cooling since the toroidal tray 30A is housed in a virtually airtight enclosure, with resultant low cooling cost.

Figure 15:
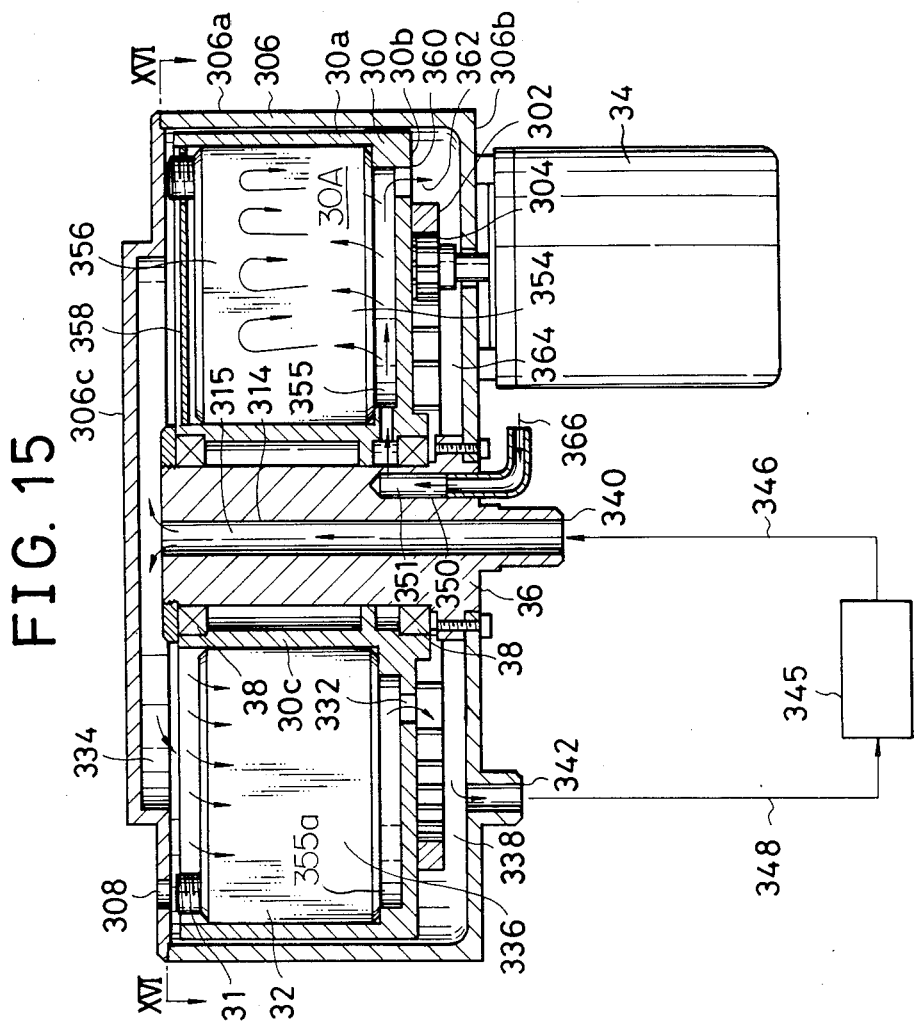
FIG. 15 is a cross-sectional view of a temperature control system for the reagent table of the automatic analysis apparatus according to the present invention.
Figure 16:
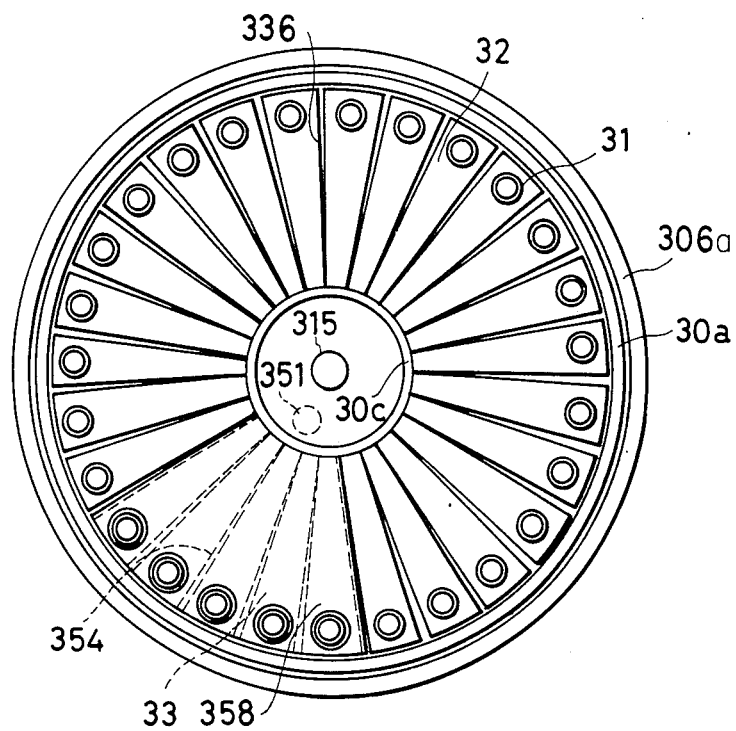
FIG. 16 is a view taken along the line XVI—XVI of FIG. 15.
Figure 17:
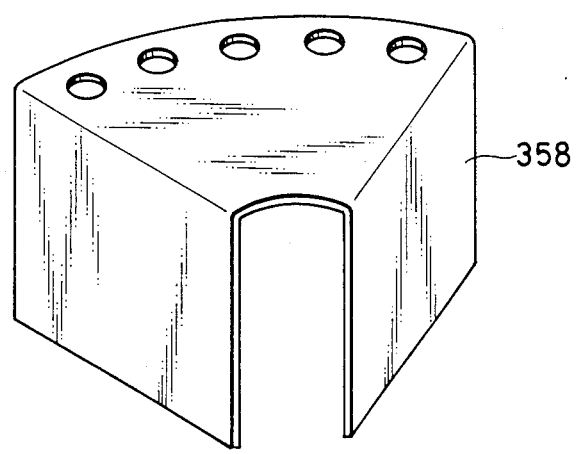
FIG. 17 is a shielding partition for the temperature control system of FIG. 15.

Referring to FIGS. 15 through 17, a modification of the cooling means of FIGS. 12 through 14 will be described. Although most reagent requires strict temperature control for desired reaction with the sample with which it is mixed, different reagents 32 must be kept at different levels of temperature. For example, enzymatic reagents need to be maintained at 2° to 10° C. while others, if cooled too excessively, tend to lose their activity in reaction or cristalize. When different reagents requiring control at different temperature levels have to be carried on a reagent table at the same time, provision must be made to give separate temperature control.

To this aim, the toroidal tray 30A is divided into two portions, one of which is kept at room temperature and reagents which should be maintained at room temperature are stored in this portion. The other portion is connected to the cooling means 345 for cooling reagents which required to be cooled at low temperatures.

A sectorial shell 358, preferably shaped as in FIG. 17 made of a heat insulating material, is provided, which, having the substantially same radius as the circular side wall 30a of the toroidal tray 30A, is fitted snugly within the tray, as illustrated in FIG. 16 to isolate a group of containers 33 containing a first reagent to be maintained at room temperature. The rest of reagent containers 32 in the tray 30A each contain a second reagent to be cooled to low temperature as by means of the cooling means 345.

A second vertical passage 351 is defined in the vertical column 36 to open to the atmosphere through an inlet port 366 provided at the lower end of the passage. Connected to the passage 351 is a space 355 defined below the bottom of the containers 33 through a vertical opening formed along the inner periphery of the shell 358. In that part of the bottom plate 30b falling beneath the containers 33 are defined a number of throughholes 360 to intercommunicate the space 355 and gaps 354 defined between the side walls of the containers 33.

Referring to FIG. 15, the cooled air from the cooling means 345 first enters the vertical central passage 315 through an inlet 340, moving into the space 334 defined between the top cover 306 and the top of the reagent containers 32 in the tray 30A and then through the gaps between the sides of adjacent containers 32 into the space 355 formed between the bottom of the containers 32 and bottom plate 30b. The air leaving the space 355a enters the bottom space 338 defined between the bottom plate 30b and the bottom 306b of the tray 30A through holes 331 in the bottom plate 30b before exiting the tray 30A through the vent hole 342 to return to the cooling means 345 through the return line 348. In this particular embodiment, the cooling occurs in the leftside of the toroidal 30A in FIG. 5. The numeral 332 indicates in the form of an arrow the direction of air flow.

In this manner, the reagent vessels 33 are placed in a circulation of ambient air, indulated in the shell 358 from the cooled environment in which the rest of reagent containers 32 are placed under low temperature control.

Many modifications and variations of the present invention are possible in light of the above teachings. It is, therefore to be understood that the scope of this invention should not be limited to the above description and accompanying drawings, but protected by the appended claims.

What is claimed is:
1. An automatic analysis apparatus comprising:
  A. a sample table rotatably disposed for rotation about a vertical axis and including a first plurality of sample containers for containing samples, a second plurality of diluted sample containers for containing diluted samples, and a third plurality of emergency samples, said first, second and third pluralities being arranged in concentric and ordered circular rows for sequential operation, said sample table being operatively connected to first drive means which rotates said sample table in a stepping manner to bring said pluralities of containers sequentially to a separate predetermined aspiration position in each said row,
  B. a reaction table rotatably disposed for rotation about a vertical axis and mounted around said sample table, said reaction table including a plurality of reaction vessels arranged in ordered circular row for sequential operation and concentrically of said rows of said containers on said sample table, said reaction table being operatively connected to second drive means which rotates said reaction table in a stepping manner to bring said reaction vessels sequentially to a predetermined first discharge position,
  C. at least a pair of reagent tables each rotatably disposed for rotation about a vertical axis and situated externally of said reaction table, each said reagent table including a plurality of identical reagent containers of sectional cross section for containing at least one type of reagent, said containers being laid out in a circular pattern, each said reagent table being operatively connected to separate drive means which rotates said associated reagent table in a stepping manner to bring said reagent containers sequentially to a predetermined reagent pipetting position,
  D. sample pipetting means provided mounted adjacent to said reaction table and including a stationary cleaning trough and a pair of first and second identical pipetting tubes fixedly secured to both ends of a linear arm that is horizontally rotatably pivoted at its center on a stationary vertical column and drive means which moves said linear arm about said vertical column to bring each paired pipetting tube first to said aspiration position for said sample containers where a measured aliquot of sample is picked up, then to said first discharge position where the picked up sample aliquot is discharged, and finally to said cleaning trough where said pipetting tubes are cleaned of the sample residue for the next round of operation, said paired pipetting tubes being operated by drive means to be alternatively employed in such a manner that, when one of said paired pipetting tubes is at said first discharged, the other stands at said cleaning trough, said linear arm being slidably disposed for sliding movement in longitudinal direction with respect to said vertical column and connected to a power transmission system which slides said linear arm to extend each said pipetting tube from said aspiration position for said sample containers to a diluted or emergency sample container that is situated radially externally of said aspiration position so that a measured aliquot of diluted or emergency sample can be picked up for transfer to said discharge position for testing purposes,
  E. reagent pipetting means provided mounted between said reaction table and each reagent table and consisting of a cleaning trough, a pair of first and second identical reagent pipetting tubes fixedly secured to both ends of a linear arm that is horizontally rotatably pivoted at its center on a stationary vertical column, and drive means which moves said linear arm about said vertical column to turn each said paired reagent pipetting tubes first to said reagent pipetting position where a measured aliquot of reagent is picked up, then to a second discharge position situated a predetermined number of steps after said first discharge position where the picked up aliquot of reagent is discharged to mix with the picked up aliquot of sample discharged at said first discharge position to produce a reaction mixture in said reaction vessel so that the mixture is eventually allowed to cause reaction for subsequent analytical purposes,
  F. a photometric system for biochemical and EIA analysis of the mixture, comprising a bead feeder consisting of a bead disk rotatably disposed for rotation about a vertical axis and mounted adjacent to said reaction table, a number of bead stockers mounted at circumferential locations along the periphery of said bead disk and each adapted to contain beads, drive means which rotates said bead table to bring said stockers sequentially to a predetermined bead supply position, and a feeding level provided on each stocker which is actuated through an electromagnetic solenoid to open said stockers at said bead supply position to supply beads into the mixture to a predetermined bead level, a frame or largely U-shaped cross section mounted in said reaction table at said bead supply position and vertically movable disposed between an upper position where one of said reaction vessels at said bead supply position is snugly housed in said frame and a lower position where said reaction vessel is lowered away from said frame, a light source provided mounted at a fixed position internally of said bead supply position and adapted to produce a predetermined wavelength of light beam that traverses through the mixture along a path below said bead level when said frame is at said lower position, sensor means provided mounted opposite said light source and oriented to receive said light beam after passage through the mixture to detect changes in said light beam compared with said wavelength, and a built-in optical system assembled into said frame and consisting of a set of reflectors so arranged that, when said frame is at said upper position, said light beam is allowed to reflect and pass through the mixture along a path above said bead level, said optical system reflecting said light beam back to be received by said sensor, G. electrolytic analysis system for electrolytic analysis of samples on said sample table, comprising said sample pipetting means and a testing bottle situated at a position along the traveling path of said sample pipetting tubes, said sample pipetting tubes being operated to pick up a measured aliquot of sample from said first, second and third pluralities of containers to discharge into said testing bottle for eleclrolytic analysis, and H. fluorescent analysis for fluorescent analysis of samples on said sample table by measuring the density of chemicals container therein, comprising a light source provided mounted at a fixed position in said sample table and adapted to produce a predetermined wavelength of light beam that traverses through the sample in one of said first plurality of sample containers that is rotated to a predetermined scanning position, and sensor means provided mounted opposite said scanning position to receive said light beam after passage through said sample container to detect changes in said light beam compared with said wavelength.

2. An automatic analysis apparatus as set forth in claim 1, wherein each said reagent table comprising a housing of largely cylindrical shape consisting of a circular external wall, a top cover and a bottom place, a stationary vertical central column provided to support said housing in fixed position and running through the center of said housing, a torous tray rotatably disposed in said housing and adapted to contain said reagent containers in said ciruclar pattern, said torous tray consisting of a cylindrical external wall and a bottom wall, said torous tray being mounted in said housing such as to form a top space between said top cover and said containers and a bottom space between said bottom wall of said torous tray and said bottom plate of said housing, said torous tray being operatively connected to said drive means which rotates said tray to bring said containers sequentially to said pipetting position, and a cooling system adapted to keep said containers at low temperature and comprising a passage defined in said vertical column of said housing through the central axis thereof, a supply line interconnected between said cooling system and an inlet formed at a lower end of said passage, a supply port formed at an upper end of said passage and opened into said top space, bottom holes formed in said bottom wall of said torous tray, an exit port formed in said bottom plate of said housing, and a return line interconnected between said exit port and said cooling device for recirculation of said cooling medium, whereby said cooling medium after leaving said passage moves from said top space to said bottom space through the gaps of said adjacent containers.

3. An automatic analysis apparatus as set forth in claim 1, wherein said tray includes a largely closed shell of sectorial shape adapted to contain a group from said containers which has to be stored at room temperature, isolated from the rest which is cooled by said cooling system, said shell comprising an eccentric vertical passage defined in said vertical column of said housing, an inlet formed at a lower end of said eccentric passage and opened to the atmosphere, a supply port formed at an upper end of said eccentric passage and opened into said shell through an upper vent hole formed in an upper end of said shell, lower vent holes formed in a bottom wall of said shell, and exit holes formed in said bottom wall of said torous tray, whereby atmospheric air through said eccentric passage is allowed to pass through the gaps of said group of reagent containers in said shell so as to keep said group at room temperature.

4. An automatic analysis apparatus as set forth in claim 1, wherein each reagent pipetting means includes a pair of agitator means affixed adjacent to said paired reagent pipetting tubes, respectively, adapted to stir the mixture at a predetermined stirring position situated at a predetermined number of steps after said second discharge position so that the mixture, after having prepared by one of said reagent pipetting tubes at said second discharge position, is blended into a homogeneous state to allow the mixture to cause proper reaction, each agitator means comprising an air pump and a nozzle operatively connected to said air pump through an air line, said nozzle being submerged into the mixture when said air pump is energized.

* * * * *